(12) United States Patent
Wheeler et al.

(10) Patent No.: US 8,845,641 B2
(45) Date of Patent: Sep. 30, 2014

(54) EXPANDABLE ARTHROPLASTY PLATES

(75) Inventors: Brad Wheeler, Greenwood, IN (US);
Adam M. Griner, Columbia City, IN (US); Vincent A. Webster, Warsaw, IN (US); Rebecca Parrott, Winona Lake, IN (US); Shaun R. Cronin, Warsaw, IN (US); Bart C. Benedict, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 510 days.

(21) Appl. No.: 13/126,809

(22) PCT Filed: Oct. 30, 2009

(86) PCT No.: PCT/US2009/062793
§ 371 (c)(1),
(2), (4) Date: Jul. 11, 2011

(87) PCT Pub. No.: WO2010/051457
PCT Pub. Date: May 6, 2010

(65) Prior Publication Data
US 2011/0264154 A1 Oct. 27, 2011

Related U.S. Application Data

(60) Provisional application No. 61/110,177, filed on Oct. 31, 2008.

(51) Int. Cl.
*A61B 17/56* (2006.01)
*A61B 17/16* (2006.01)
*A61B 19/00* (2006.01)
*A61F 2/46* (2006.01)

(52) U.S. Cl.
CPC ......... *A61F 2/4657* (2013.01); *A61B 2019/461* (2013.01); *A61F 2002/4658* (2013.01); *A61B 17/1671* (2013.01); *A61B 19/46* (2013.01)
USPC ........................................ 606/86 R

(58) Field of Classification Search
CPC .. A61B 17/56; A61B 2019/461; A61B 19/46; A61B 17/1764; A61B 17/1767
USPC ........ 606/86 R, 102; 623/17.11–17.16, 20.29
See application file for complete search history.

(56) References Cited

U.S. PATENT DOCUMENTS 8,137,401 B2 * 3/2012 Stad et al. .................. 623/17.11
2004/0122439 A1 6/2004 Dwyer et al.
(Continued)

FOREIGN PATENT DOCUMENTS

EP 0860143 A2 8/1998

OTHER PUBLICATIONS

International Preliminary Report on Patentability mailed May 12, 2011 in the related International Application No. PCT/US2009/062793.

*Primary Examiner* — Christopher Beccia
(74) *Attorney, Agent, or Firm* — Schwegman Lundberg & Woessner, P.A.

(57) ABSTRACT

A device (20) used during a medical procedure to engage a cross-section of a bone is disclosed herein. The device is selectively expandable to correspond to the cross-section of the bone. Once the device is properly sized, the device is used as a sizing tool to select the proper size of an implant or as a surgical guide for preparing the bone with a surgical instrument, for example.

25 Claims, 13 Drawing Sheets

(56) References Cited

U.S. PATENT DOCUMENTS

| | | | |
|---|---|---|---|
| 2005/0203541 A1* | 9/2005 | Steffensmeier et al. | 606/102 |
| 2005/0261769 A1* | 11/2005 | Moskowitz et al. | 623/17.11 |
| 2005/0267485 A1 | 12/2005 | Cordes et al. | |
| 2007/0161930 A1* | 7/2007 | Reitzig et al. | 600/594 |

* cited by examiner

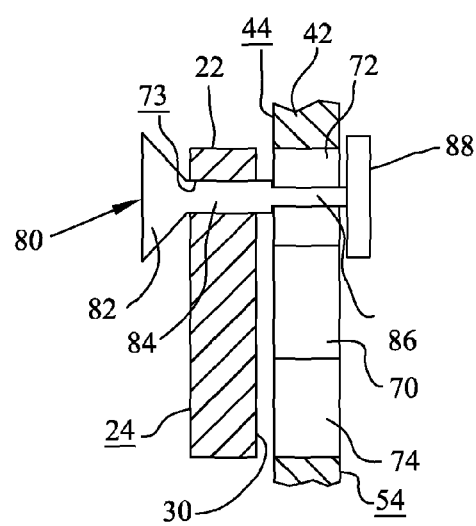
FIG. 1E
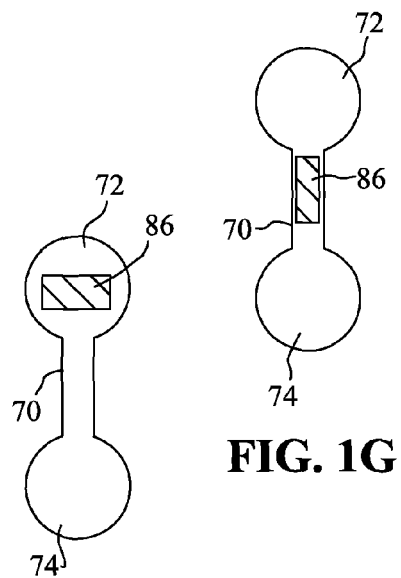
FIG. 1F
FIG. 1G
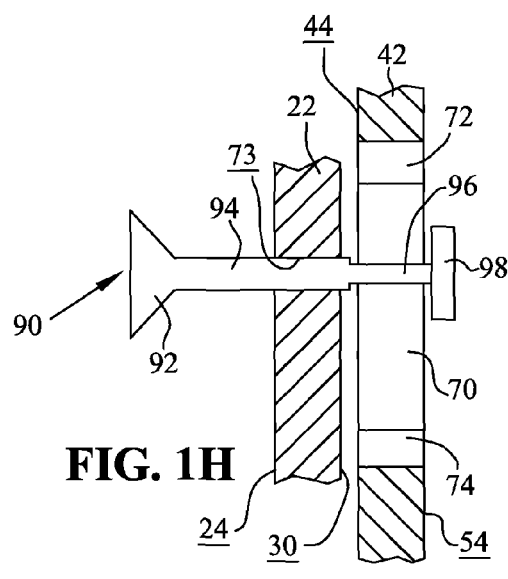
FIG. 1H
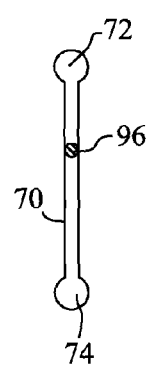
FIG. 1I

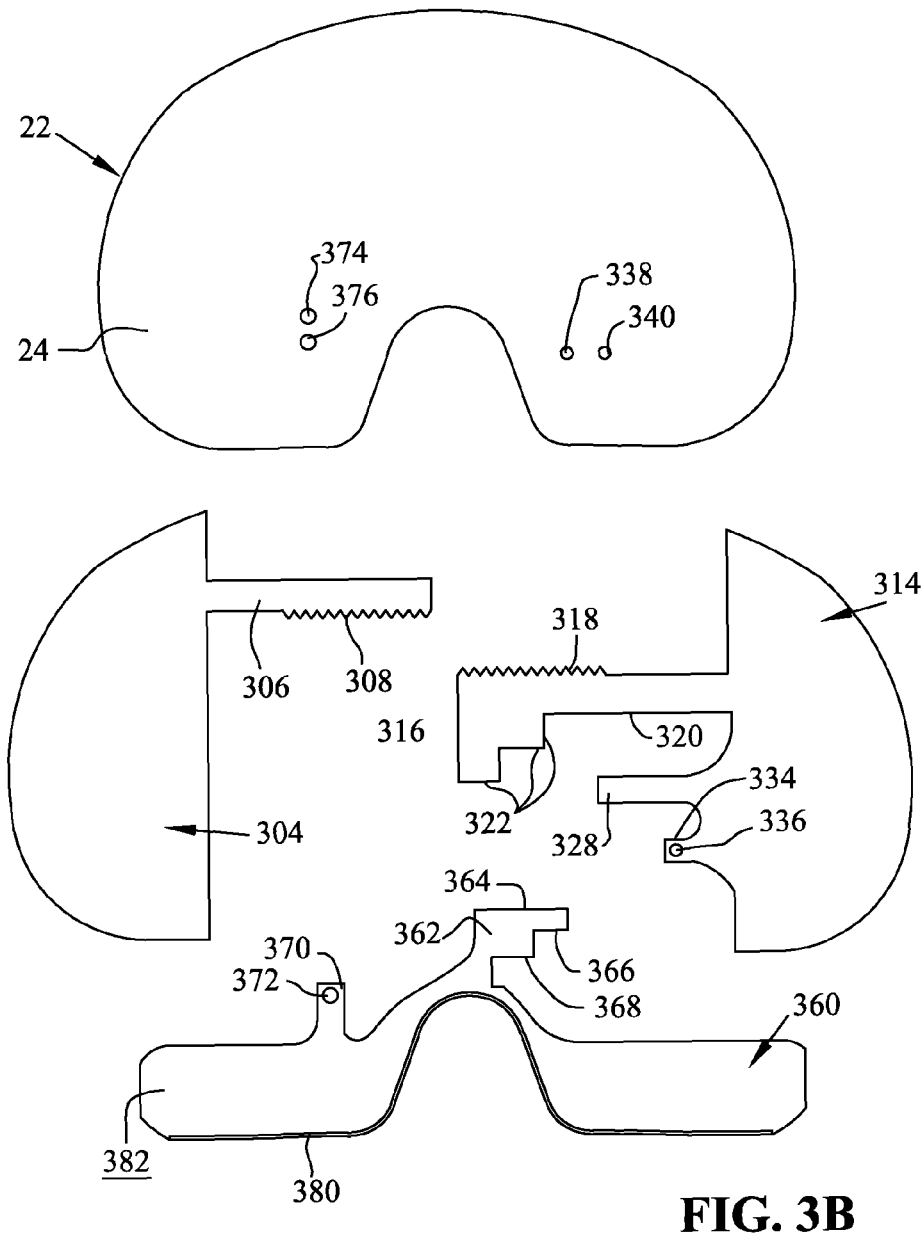
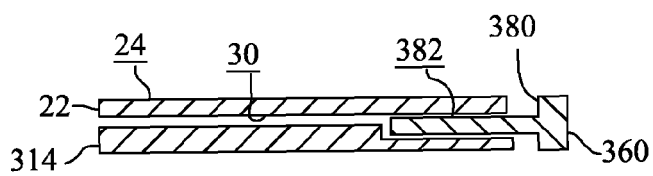
FIG. 3B
FIG. 3C

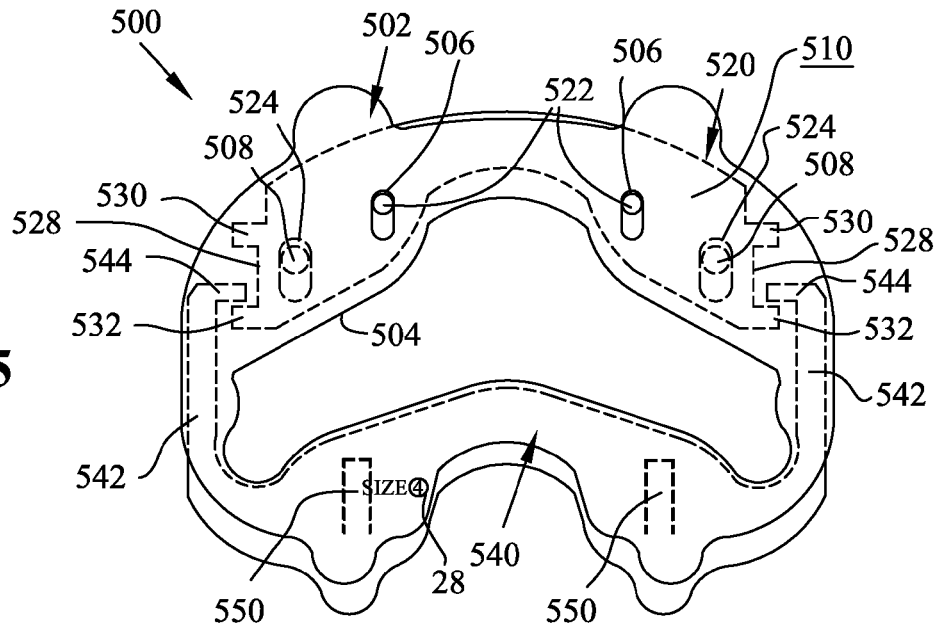
FIG. 5
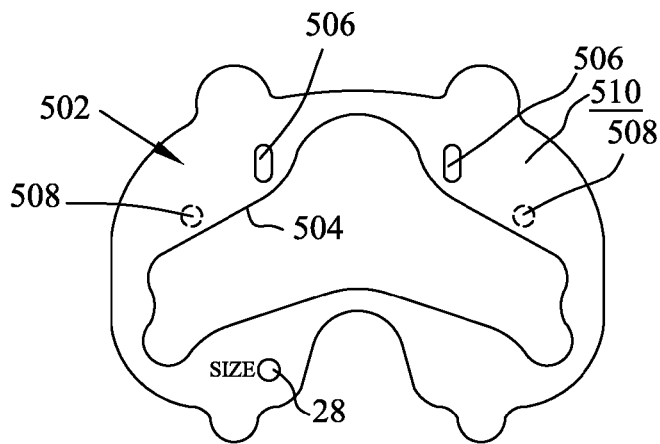
FIG. 5A
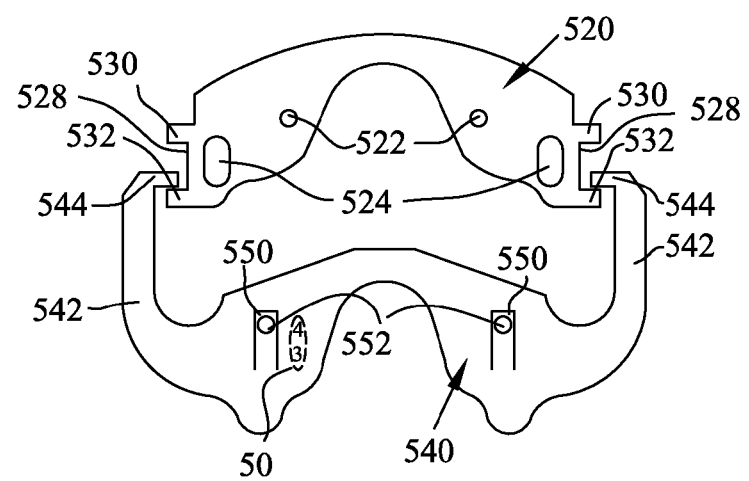

EXPANDABLE ARTHROPLASTY PLATES

BACKGROUND

1. Field of the Invention

The present disclosure relates to a device that is selectively expandable, and to a method of using the device to perform an arthroplasty procedure.

2. Description of the Related Art

Arthroplasty plates are generally used to size instruments and prostheses and also to prepare bones for the addition or provision of prostheses. Arthroplasty plates may include, for example, tibia plates such as provisional and sizing plates. After resection, tibia plates may be positioned on a cross-section of the resected bone to determine, or identify, the proper size of an implant, or to facilitate preparation of a bone with suitable instruments, i.e. a surgical broach, to receive a prosthesis. A surgical kit includes a plurality of plates corresponding to a plurality of sizes. Plates are positioned on the bone sequentially until a properly fitting plate is identified. It is desirable to limit the number of plates required to perform such procedures.

SUMMARY

Exemplary embodiments of an adjustable device and a method of using the adjustable device are disclosed herein.

In one embodiment, a device is provided for use during a surgical procedure to engage a cross-section of a bone, the cross-section of the bone having an anterior/posterior dimension and a medial/lateral dimension. The device includes a first member having an engaging surface configured to rest against the cross-section of the bone and a second member coupled to the first member, the first member and the second member cooperating to define a height and a width of the device. The device also includes adjustment means for adjusting at least one of the height of the device to correspond to the anterior/posterior dimension of the cross-section of the bone and the width of the device to correspond to the medial/lateral dimension of the cross-section of the bone.

In another embodiment, a device is provided for use during a surgical procedure to engage a cross-section of a bone, the cross-section of the bone having an anterior/posterior dimension and a medial/lateral dimension. The device includes a first member having an engaging surface configured to rest against the cross-section of the bone and a second member coupled to the first member, the device having a first configuration in which the first and second members cooperate to define a first dimension measured in a direction parallel to the engaging surface and a second configuration in which the first and second members cooperate to define a second dimension measured in the same direction as the first dimension, the second dimension of the device differing from the first dimension of the device and equaling one of the anterior/posterior dimension and the medial/lateral dimension of the cross-section of the bone, whereby the device in the second configuration corresponds to at least one of the anterior/posterior dimension and the medial/lateral dimension of the cross-section of the bone.

In yet another embodiment, a method is provided for performing a surgical procedure on a cross-section of a bone, the cross-section of the bone having an anterior/posterior dimension and a medial/lateral dimension. The method includes the steps of providing a device including a first member and a second member, the first member and the second member cooperating to define an outer perimeter of the device, positioning an engaging surface of the device against the cross-section of the bone, and adjusting the outer perimeter of the device to correspond to at least one of the anterior/posterior dimension of the cross-section of the bone and the medial/lateral dimension of the cross-section of the bone.

BRIEF DESCRIPTION OF THE DRAWINGS

The above-mentioned and other features of the disclosure, and the manner of attaining them, will become more apparent and will be better understood by reference to the following description of embodiments of the disclosure taken in conjunction with the accompanying drawings, wherein:

FIGS. 1A to 1I are sectional and plan views of the adjustable device of FIG. 1 and exemplary adjustment means for adjusting a dimension of the expandable device of FIG. 1;

FIGS. 3B and 3C are exploded and sectional views of the adjustable device of FIG. 3;

FIG. 5 is a plan view of another exemplary embodiment of an adjustable device for adjusting a dimension of the adjustable device;

FIG. 5A is an exploded plan view of the adjustable device of FIG. 5;

Corresponding reference characters indicate corresponding parts throughout the several views. The exemplifications set out herein illustrate embodiments of the application and such exemplifications are not to be construed as limiting the scope of the invention in any manner.

DETAILED DESCRIPTION

An adjustable device is disclosed herein having adjustment means for adjusting the height and/or the width of the device. The adjustable device, generally, has an engagement surface for engaging a cross-section of a bone, i.e. the tibia, spaced apart from an opposite surface. The engagement surface and the opposite surface are spaced apart by a peripheral surface which defines the thickness of the adjustable device. The height of the adjustable device spans between top and bottom edges of the adjustable device, and the width of the adjustable device spans between right and left edges of the adjustable device. Accordingly, the adjustable device may have sides corresponding to said top, bottom, right and left edges. When positioned on the tibia, the height of the adjustable device corresponds to the anterior/posterior (A/P) dimension of the cross-section of the bone and the width of the adjustable device corresponds to the medial/lateral (M/L) dimension of the cross-section of the bone.

In operation, the top or bottom sides may be adjusted to change the height of the device, and the right and left sides may be adjusted to change the width of the device. In certain embodiments, adjusting either the height or the width of the device will automatically adjust the other dimension to a corresponding degree. In certain other embodiments, the height and the width may be adjusted independently. It is within the scope of the present invention that the device may be adjusted continuously or discretely. Once the device is adjusted to a desired size that corresponds to the cross-section of the bone in the A/P dimension and/or the M/L dimension, the device may be used as a sizing tool to select the proper size of an implant or as a surgical guide for preparing the bone with a surgical instrument, for example. According to an exemplary embodiment of the present invention, the adjustable device is adjusted to match or achieve the best possible fit with the cross-section of the bone in the A/P dimension and/or the M/L dimension. According to another exemplary embodiment of the present invention, the adjustable device is adjusted to span substantially the entire cross-section of the bone.

Figure 1:
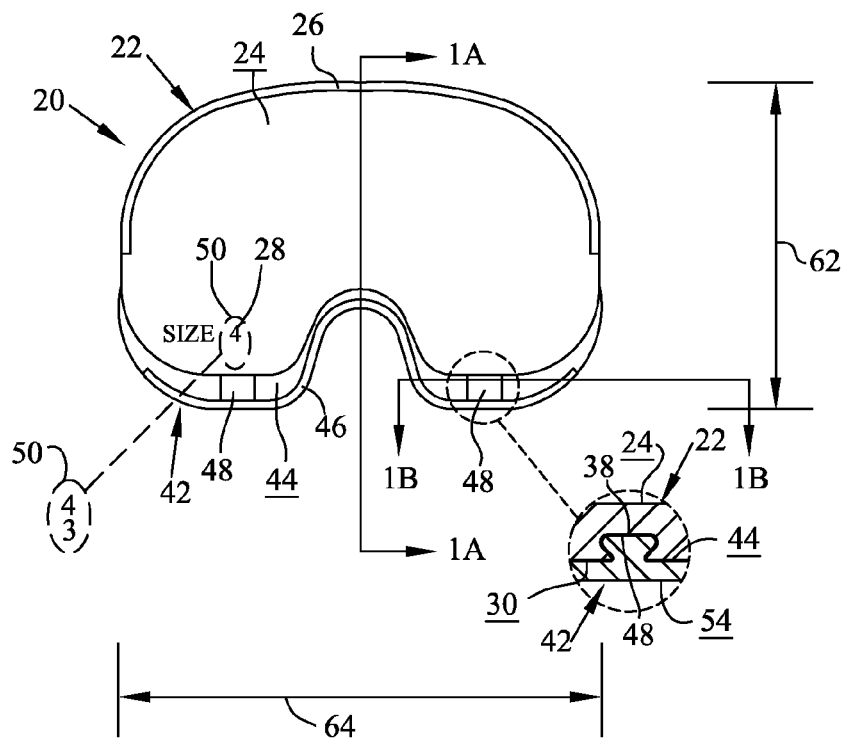
FIG. 1 is a plan view of an exemplary embodiment of an adjustable device showing a base member and a bottom member.

FIG. 1 is a plan view of an exemplary embodiment of an adjustable device 20. Adjustable device 20 comprises base member 22 and bottom member 42. Base member 22 has front surface 24 spaced apart from back surface 30 (shown in FIG. 1C) and window 28. Window 28 is an opening connecting front surface 24 and back surface 30 provided for viewing a size numeral positioned on bottom member 42. Ridge 26 may be provided on the periphery of base member 22 to create a platform for mounting an instrument or tool on adjustable device 20. As shown, ridge 26 extends perpendicularly from front surface 24 and away from back surface 30 along the right, top, and left sides of base member 22. Ridge 26 may also extend from front surface 24 and away from back surface 30 along the bottom side of base member 22 to thereby extend along the entire periphery of top surface 24. As used herein, front surface 24 is the opposite surface.

Figure 1A:
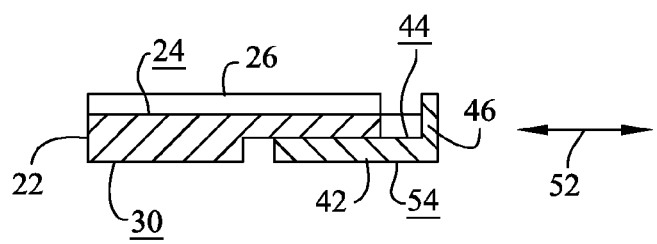
Figure 1B:
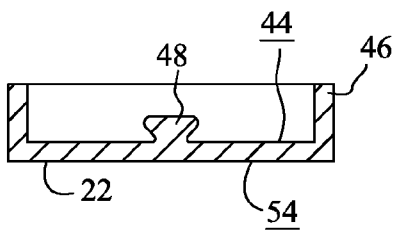
Figure 1C:
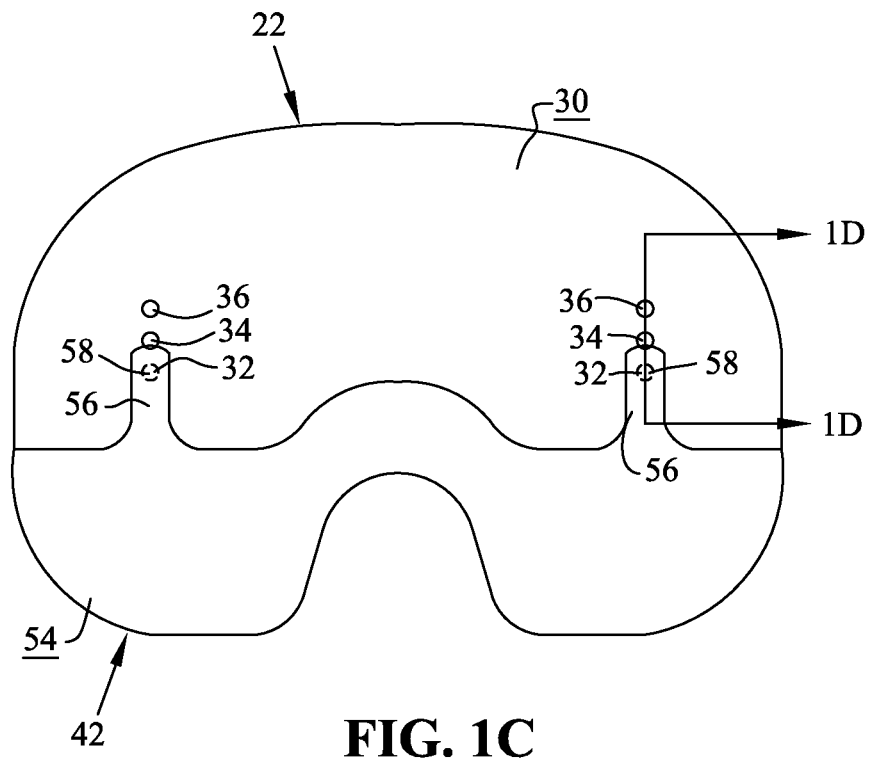
Figure 1D:
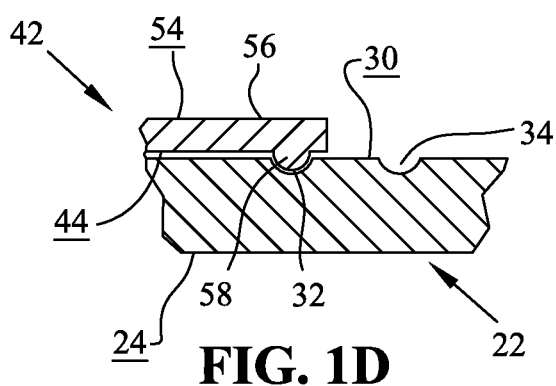

Bottom member 42 has front surface 44 (shown in FIG. 1) spaced apart from back surface 54 (shown in FIG. 1C). Bottom member 42 also includes sizing area 50 disposed on front surface 44. Sizing area 50 is provided for showing a size numeral corresponding to a plurality of adjustment dimensions, or sizes, of adjustable device 20 which are visible through sizing window 28 of base member 22. Like base member 22, bottom member 42 may further include a peripheral ridge 46. As shown, ridge 46 extends perpendicularly from front surface 44 and away from back surface 54 along the bottom side of bottom member 42. As used herein, back surface 54 is the engagement surface. In use, a practitioner may use ridge 26 and ridge 46 to pull bottom member 42 outwardly beneath base member 22 to expand height 62 of device 20.

Device 20 may comprise an adjustment means for adjusting height 62 of device 20, which may be a sliding means that maintains an orthogonal relation between base member 22 and bottom member 42 and prevents their separation. As shown in FIG. 1, sliding means may comprise a dovetail mechanism comprising a pair of dovetail rails 48 extending upwardly from top surface 44 of bottom member 42 to operably engage dovetail slots 38 in bottom surface 30 of base member 22. Bottom member 42 may slide relative to base member 22 to expand height 62 of adjustable device 20. Width 64 is also shown. The adjustment direction is shown as arrow 52 in FIG. 1A. Alternatively, other rail and slot mechanisms may be used. For example, a rail may be provided on bottom surface 30 of base member 22 with a corresponding slot positioned on top surface 44 of bottom member 42. In another embodiment, bottom member 42 may be wider than base member 22 and ridge 46 may extend along the right and left sides of bottom member 42. Ridge 46 may comprise a rail, or longitudinal protrusion, extending inwardly along its right and left sides operably coupled with slots disposed along the right and left peripheral sides of base member 22. Alternative sliding means may comprise a slot and pin arrangement whereby pins prevent separation of members and guide the direction of their motion.

Base member 22 and bottom member 42 may be continuously or discretely adjustable and may comprise sizing means for positioning base member 22 and bottom member 42 in one or more positions relative to each other. FIG. 1C shows a plan view of the back side of an embodiment of adjustable device 20 in one of three positions corresponding to three sizes. In each position, a different numeral can be observed through window 28 of base member 22 (FIG. 1). Sizing means includes three pairs of cavities 32, 34, 36, in back surface 30 of base member 22 and a pair of protrusions 58 extending from arms 56 of bottom member 42 towards back surface 30 of base member 22. Protrusions 58 penetrate, one at a time, pairs of cavities 32, 34, 36, to removably secure, or snap-lock, bottom member 42 in a desired position relative to base member 22. In FIG. 1C, protrusions 58 are shown engaging cavities 32 for providing adjustable device 20 in a first, maximum height position by extending the bottom side of bottom member 42 away from base member 22. Depending upon the particular patient, the surgeon may instead choose to position protrusions 58 in cavities 34 to provide adjustable device 20 in a second, medium height position, or the surgeon may choose to position protrusions 58 in cavities 36 to provide adjustable device 20 in a third, minimum height position. It is within the scope of the present invention that base member 22 may include more than three cavities 32, 34, 36, so that the height of adjustable device 20 may be adjusted to more than three positions.

FIGS. 1E through 1G show an alternative embodiment sizing means. FIG. 1E shows sizing means comprising apertures 72, 74, connected by slot 70 and disposed in bottom member 42, and pin 80 having first, second, third, and fourth portions 82, 84, 86, 88. First portion 82 of pin 80 is a knob for rotating pin 80. Second portion 84 of pin 80 has a circular cross-section with a diameter sized to rotatably fit in aperture 73 of base member 22. Third portion 86 of pin 80 has a rectangular cross-section with a length and a width dimension. The width dimension of third portion 86 is smaller than the length dimension of third portion 86, such that the width dimension of third portion 86 is able to fit within and slide through slot 70 and the length dimension of third portion 86 is larger than slot 70. Fourth portion 88 of pin 80 is sized larger than apertures 72, 74, and slot 70 to prevent removal of pin 80 therethrough. When pin 80 is turned such that the length dimension of third portion 86 is normal to the longitudinal axis of slot 70 (FIG. 1F), which occurs when one of aperture 72, 74, is situated substantially coincident with the longitudinal axis of pin 80, third portion 86 of pin 80 cannot enter slot 70 and bottom member 42 cannot move relative to base member 22. On the other hand, when pin 80 is turned such that the length dimension of third portion 86 is parallel to the longitudinal axis of slot 70 (FIG. 1G), third portion 86 of pin 80 can enter slot 70 and bottom member 42 can move relative to base member 22 with pin 80 traveling between apertures 72, 74. When pin 80 reaches a desired aperture 72, 74, the surgeon may rotate pin 80 by approximately 90 degrees to temporarily lock base member 22 relative to bottom member 42 (FIG. 1F). Additional apertures may be disposed along the length of slot 70 to create additional positions corresponding to additional adjustment sizes.

FIGS. 1H and 1I show another alternative embodiment sizing means. FIG. 1H shows sizing means comprising apertures 72, 74, connected by slot 70 and disposed in bottom member 42, and pin 90 having first, second, third, and fourth portions 92, 94, 96, 98. First portion 92 of pin 90 is a knob or handle for pulling or pushing pin 90. Second portion 94 has a circular cross-section with a diameter sized to translate within aperture 73 of base member 22, so that pin 90 can slide towards or away from bottom member 42. Third portion 96 of pin 90 has a circular cross-section with a diameter smaller than the diameter of second portion 94 of pin 90. Third portion 96 of pin 90 is configured to fit within and slide through slot 70. Fourth portion 98 of pin 90 is sized larger than apertures 72, 74, and slot 70 to prevent removal of pin 90 therethrough. When pin 90 is pushed towards bottom member 42, the thicker second portion 94 of pin 90 extends through bottom member 42. In this locked position, because the thicker second portion 94 of pin 90 cannot enter slot 70, bottom member 42 cannot move relative to base member 22. On the other hand, when pin 90 is pulled away from bottom member 42 (FIG. 1H), third portion 96 of pin 90 extends through bottom member 42. In this unlocked position, because third portion 96 of pin 90 can enter slot 70, bottom member 42 can move relative to base member 22 with pin 90 traveling between apertures 72, 74. When pin 90 reaches a desired aperture 72, 74, the surgeon may again push pin 90 to temporarily lock base member 22 relative to bottom member 42. Additional apertures may be disposed along the length of slot 70 to create additional positions corresponding to additional adjustment sizes.

Figure 1J:
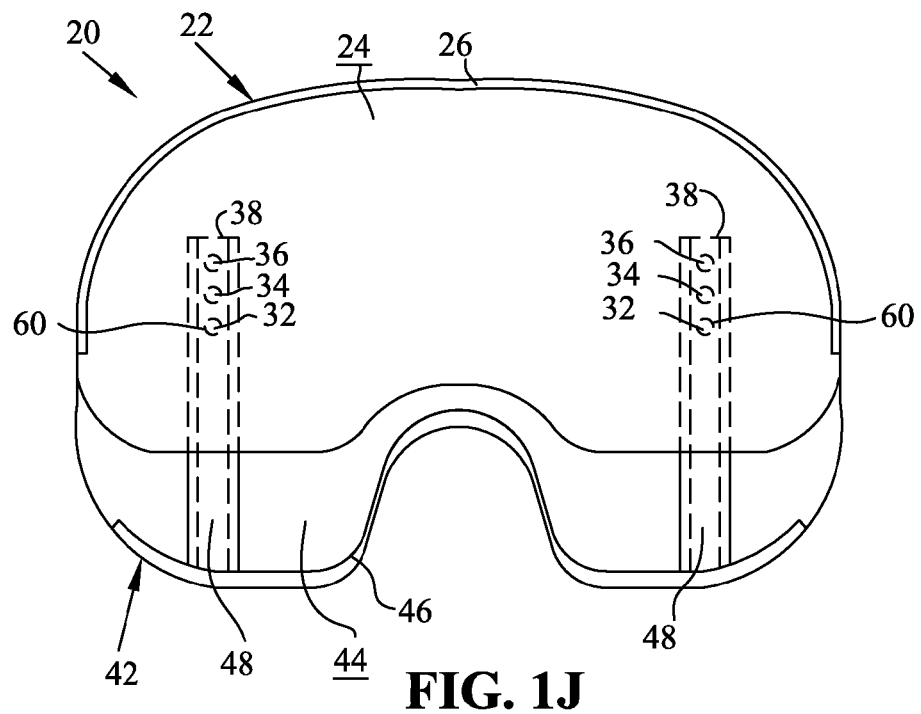
FIG. 1J is a plan view of the adjustable device of FIG. 1 showing sizing means.

FIG. 1J shows another alternative embodiment sizing means. As in FIG. 1C, sizing means includes three pairs of cavities 32, 34, 36, in back surface 30 of base member 22. Biased detent balls 60 extend from dovetail rail 48 on bottom member 42 to engage, selectively, pairs of cavities 32, 34, 36. Detent balls 60 penetrate, one at a time, pairs of cavities 32, 34, 36, to removably secure, or snap-lock, bottom member 42 in a desired position relative to base member 22. In FIG. 1J, detent balls 60 are shown engaging cavities 32 for providing adjustable device 20 in a first, maximum height position by extending the bottom side of bottom member 42 away from base member 22. Depending upon the particular patient, the surgeon may instead choose to position detent balls 60 in cavities 34 to provide adjustable device 20 in a second, medium height position, or the surgeon may choose to position detent balls 60 in cavities 36 to provide adjustable device 20 in a third, minimum height position.

Figure 2:
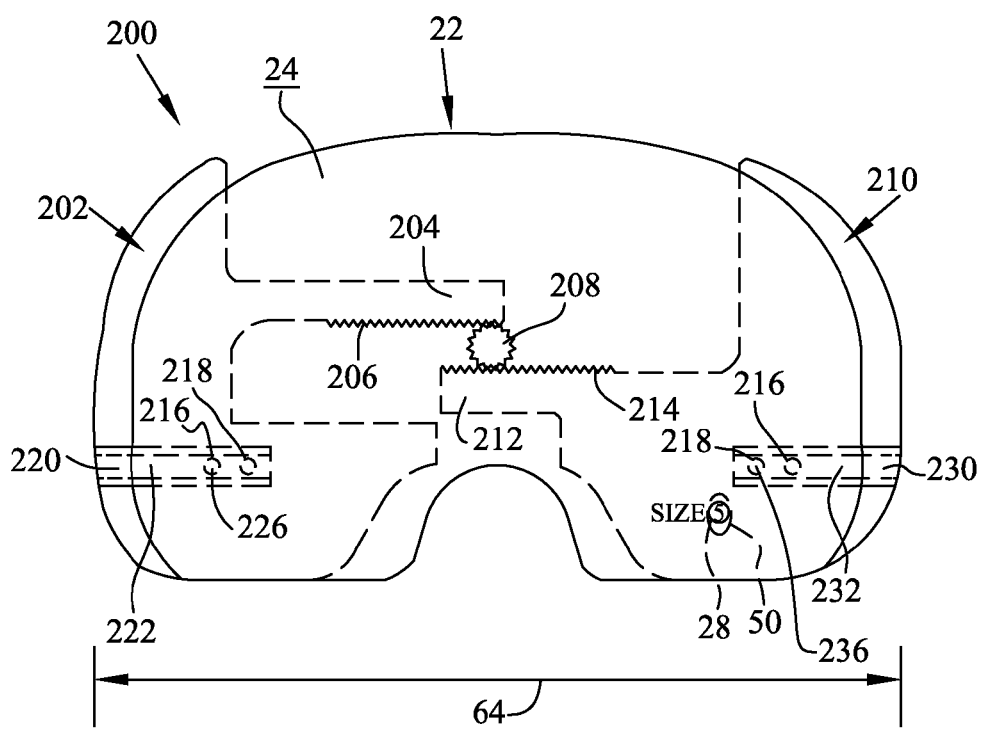
FIG. 2 is a plan view of another exemplary embodiment of an adjustable device showing the base member and right and left members.

FIG. 2 is a plan view of another exemplary embodiment of an adjustable device 200. Adjustable device 200 comprises base member 22, left member 202, and right member 210. Adjustment means are shown comprising a rack and pinion mechanism for adjusting the width of adjustable device 200. The rack and pinion mechanism comprises arm 204 extending from left member 202 substantially parallel to width dimension 64 and arm 212 extending from right member 210 substantially parallel to width dimension 64. Arms 204, 212, comprise linear racks 206, 214, respectively, for operably engaging gearwheel or pinion 208. Pinion 208 is rotatably coupled to base member 22. In operation, moving one of right or left member 202, 210, causes the respective linear rack 206, 214, to rotate pinion 208, which in turn actuates the other linear rack 206, 214, to move the other of the right or left member 202, 210.

Base member 22 and right and left members 202, 210, may comprise sliding means for maintaining an orthogonal relation between them and preventing their separation. Similarly to sliding means disclosed with reference to FIGS. 1 and 1J, sliding means may comprise a dovetail mechanism comprising dovetail rails 220, 230, extending upwardly from right and left members 202, 210, to operably engage dovetail slots 222, 232, disposed in back surface 30 of base member 22. In operation, right and left members 202, 210, may slide relative to base member 22 to expand width 64 of adjustable device 200. Alternatively, other sliding mechanisms, such as those previously described, may be used.

Base member 22 and right and left members 202, 210, may be continuously or discretely adjustable and may comprise sizing means for positioning base member 22 and right and left members 202, 210, in one or more positions relative to each other. A sizing means embodiment for placing adjustable device 200 in one of two positions corresponding to two sizes is shown. In each position, a different size indicia, i.e. numeral, can be observed through window 28. In the illustrated embodiment, the sizing means includes two pairs of cavities 216, 218, and detent balls 226, 236, which extend from dovetail rails 220, 230, to engage, selectively, pairs of cavities 216, 218. Detent balls 226, 236, penetrate, one at a time, pairs of cavities 216, 218, to removably secure, or snap-lock, right and left members 202, 210, in a desired position relative to base member 22. In FIG. 2, detent balls 226, 236, are shown engaging cavities 216 for providing adjustable device 20 in a first, maximum width position by extending the sides of right and left members 202, 210, from base member 22. Depending upon the particular patient, the surgeon may instead choose to position detent balls 226, 236, in cavities 218 to provide adjustable device 200 in a second, minimum width position.

Figure 2A:
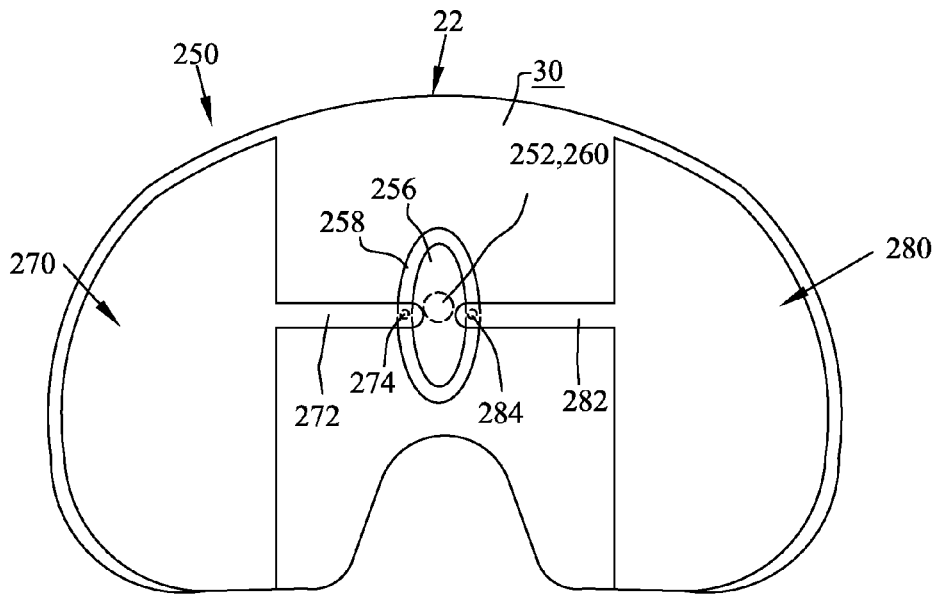
FIGS. 2A and 2B are plan views of yet another embodiment of an adjustable device for adjusting two dimensions of the adjustable device.
Figure 2B:
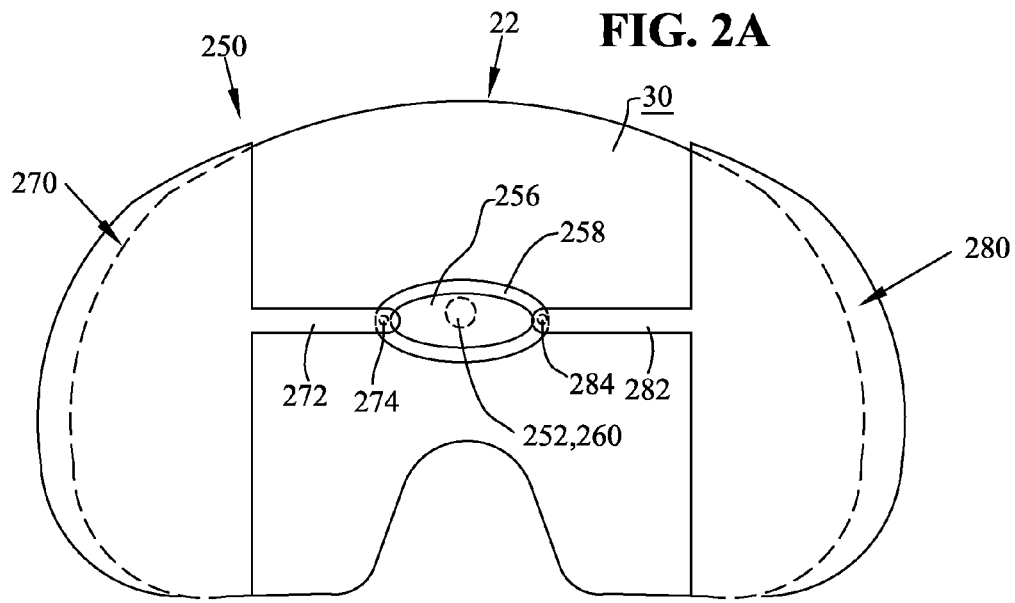

FIGS. 2A and 2B are plan views of another exemplary embodiment of an adjustable device 250 shown in two positions. Adjustable device 250 comprises base member 22, left member 280, and right member 270. Adjustment means are shown comprising an oval rotating slot mechanism for adjusting the width of adjustable device 250. The rotating slot mechanism comprises rotating member 256 having oval slot 258 disposed along its periphery. Arms 272, 282, extend from right and left members 270, 280, respectively. Arms 272, 282, include pins 274, 284, extending therefrom to be received with oval slot 258. As rotating member 256 rotates, slot 258 also rotates, and the distance between opposing slot surfaces changes. As a result, the distance between pins 274, 284, also changes to move right and left members 270, 280. As shown in FIGS. 2A and 2B, aperture 252 is provided in base member 22 to engage shaft 260 of rotating member 256 from the front side of adjustable device 250 (not shown). Shaft 260 may include a key for removably engaging a tool (not shown) used by a medical practitioner to adjust the width 64 of adjustable device 250. Sliding and sizing means may be provided as previously disclosed. Optionally, peripheral ridges may also be provided on right and left members 270, 280, to facilitate manual gripping and width adjustment.

Figure 3:
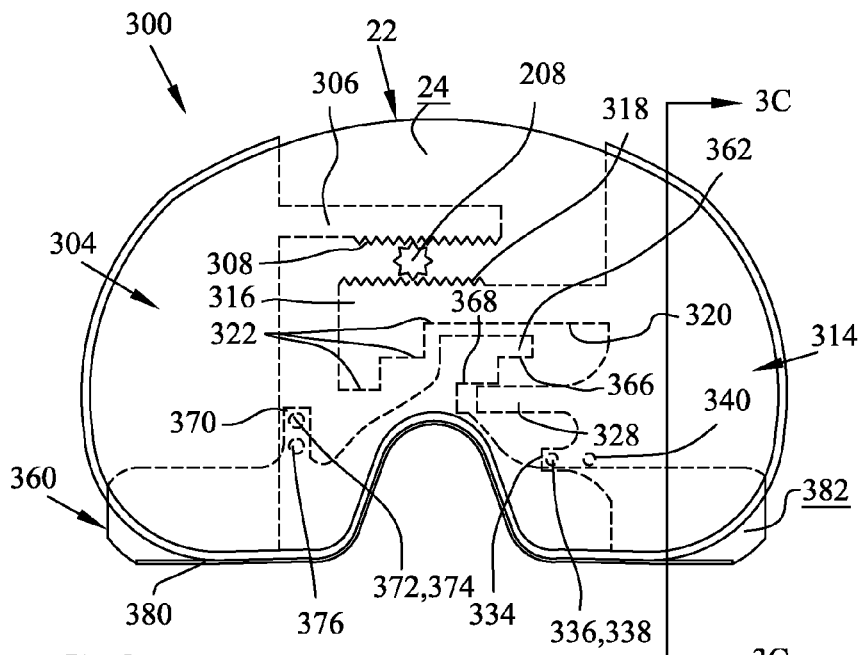
FIGS. 3 and 3A are plan views of another exemplary embodiment of an adjustable device in a first position and a second position.
Figure 3A:
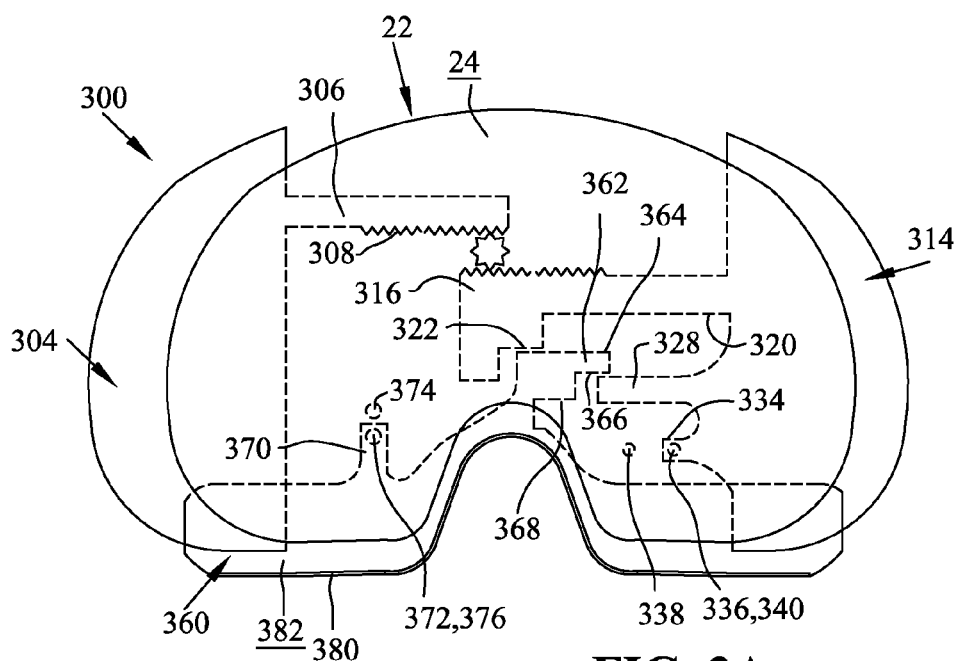

FIGS. 3 and 3A are plan views of yet another exemplary embodiment of an adjustable device 300 shown in two positions. FIGS. 3B and 3C are exploded and sectional views of the adjustable device 300 of FIG. 3. Adjustable device 300 comprises base member 22, left member 304, right member 314, and bottom member 360. Adjustment means are shown comprising a rack and pinion mechanism for adjusting the width of adjustable device 300 in a manner similar to that shown with reference to FIG. 2. The rack and pinion mechanism comprises arm 306 extending from left member 304 and arm 316 extending from right member 314. Arms 306, 316, comprise linear racks 308, 318, respectively, for operably engaging gearwheel or pinion 208. In operation, moving one of right or left member 304, 314, causes the respective linear rack 308, 318, to rotate pinion 208, which in turn actuates the other linear rack 308, 318, to move the other of the right or left member 304, 314. As previously described with reference to FIGS. 1 and 2, adjustable device 300 may include a window (not shown) for viewing a size numeral positioned in one of left and right members 304, 314, and bottom member 360. Also, adjustable device 300 may include a sliding means for maintaining an orthogonal relation between right, left and bottom members 304, 314, 360 and preventing their separation. It is also within the scope of the present invention that any or all of the components of adjustable device 300 may include peripheral rims. For example, in the illustrated embodiment, bottom member 360 includes ridge 380 extending perpendicularly from front surface 382 along the bottom edge of bottom member 360.

Adjustable device 300 may also comprise sizing means. In the embodiment shown, sizing means include means for sizing both the height and width of adjustable device 300. Width sizing means includes arms 334, 328, extending from right member 314. Arm 334 has detent ball 336 for engaging cavities 338, 340, disposed on bottom surface 30 of base member 22. In FIG. 3, detent ball 336 is shown engaging cavity 338. Arm 328 is sized and configured to engage arm 362 of bottom member 360. In the first position, shown in FIG. 3, arm 328 engages surface 368 of bottom member 360 and prevents bottom member 360 from extending downwardly. Surface 320 of arm 316 may further prevent upward movement of bottom member 360. When right member 314 slides rightwardly into the second position, shown in FIG. 3A, arm 328 disengages surface 368 and enables bottom member 360 to slide downwardly until arm 328 engages surface 366. Arm 316 further includes a plurality of surfaces 322 which cooperate with bottom member 360 to enable its movement. As shown and described, bottom member 360 has one position, retracted, when right and left members 304, 314, are retracted and adjustable device 300 is in the first position. Bottom member 360 has a second position, extended, when right and left members 304, 314, are extended. Arms 316, 328, 362, may be configured in any number of geometric configurations adapted to define movement relationships between right and left members 304, 314, and bottom member 360. In some embodiments, bottom member 360 may be placed in two positions for each width size, thereby enabling greater height adjustment relative to width adjustment.

Figure 4:
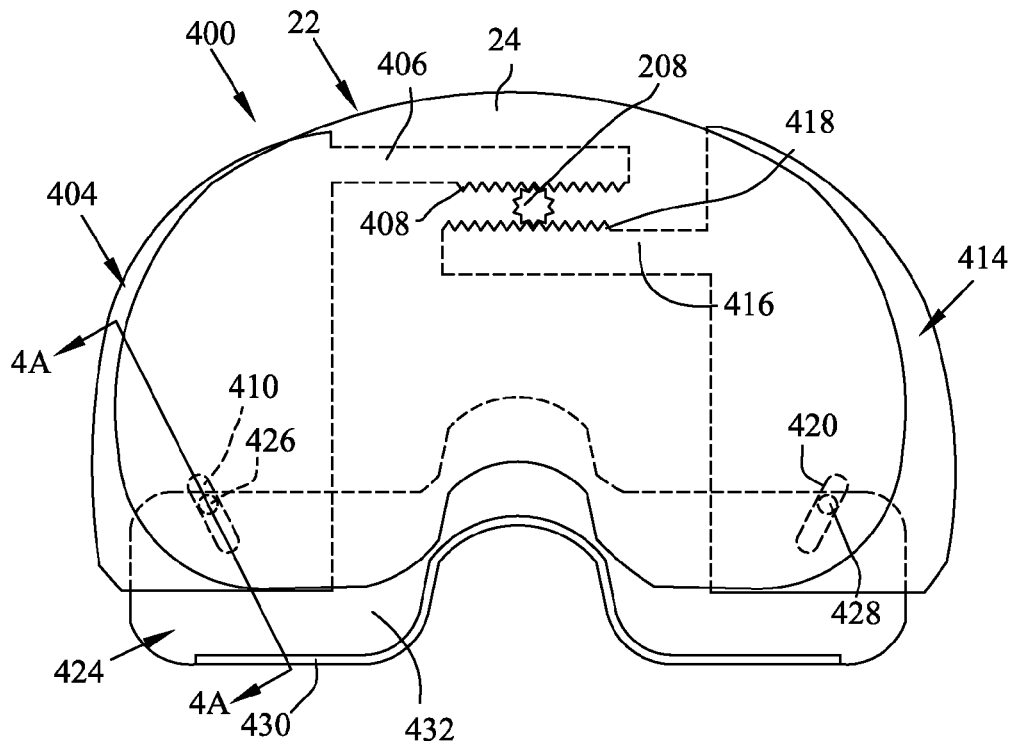
FIG. 4 is a plan view of another exemplary embodiment of an adjustable device for adjusting two dimensions of the adjustable device.

FIG. 4 is a plan view of still another exemplary embodiment of an adjustable device 400 showing another adjustment mechanism defining movement relationships between members to adjust dimensions of adjustable device 400. Adjustable device 400 comprises base member 22, left member 404, right member 414, and bottom member 424. Adjustment means are shown comprising a rack and pinion mechanism for adjusting the width of adjustable device 400 in a manner similar to that shown with reference to FIG. 2. The rack and pinion mechanism comprises arm 406 extending from left member 404 and arm 416 extending from right member 414. Arms 406, 416, comprise linear racks 408, 418, respectively, operably engaging gearwheel 208. Movement of one of right or left members 404, 414, causes the corresponding linear rack 408, 418, to rotate pinion 208, which then actuates the other linear rack to move the other member. Ridge 430 is shown extending perpendicularly front surface 432 of bottom member 424.

Adjustable device 400 may also comprise any sizing means previously disclosed. For example, as previously described with reference to FIGS. 1 and 2, adjustable device 400 may include a window (not shown) for viewing a size numeral (not shown) positioned on one of left and right members 404, 414, and bottom member 424.

Figure 4A:
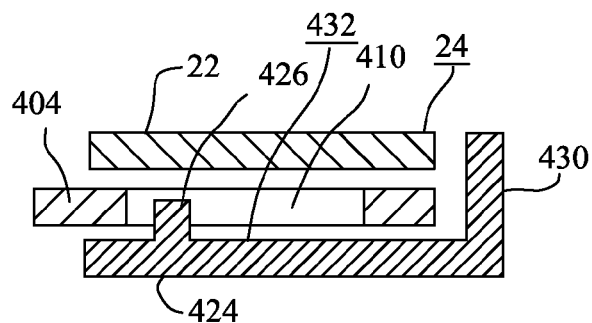
FIG. 4A is a sectional view of the adjustable device of FIG. 4.

Adjustable device 400 may comprise sliding means for maintaining an orthogonal relation between right, left and bottom members 404, 414, 424, and preventing their separation. As shown in FIG. 4A, adjustable device 400 includes slots 410, 420, and protrusions 426, 428, that extend from surface 432 of bottom member 424 into corresponding slots 410, 420. Slots 410, 420, have a longitudinal dimension shown at an angle of about 60 degrees from the width dimension. As shown in FIG. 4, as right and left members 404, 414, slide outwardly, slots 410, 420, also slide outwardly, forcing protrusions 426, 428, of bottom member 424 to slide downwardly through slot 410. As a result, bottom member 424 slides downwardly to continue the outward expansion of adjustable device 400. Similarly, bottom member 424 slides upwardly when right and left members 404, 414, slide inwardly.

FIG. 5 is a plan view of another exemplary embodiment of an adjustable device 500. Adjustable device 500 comprises base 502, top member 520, and bottom member 540. FIG. 5A is an exploded view of adjustable device 500. Base member 502 includes aperture 504 and slots 506 which are sized and configured to provide access to apertures 522 in top member 520. Aperture 504 is sized and configured to guide the action of a medical tool or instrument such as a broach having a coupling portion for engaging apertures 522. The coupling portion passes through slots 506 to engage apertures 522, thereby coupling the medical instrument to adjustable device 500. The engagement of the coupling portion of the medical instrument to apertures 522 provides support and partially restricts the movement of the medical instrument. Base member 502 also includes pins 508 extending away from the surface opposite front surface 510 which are sized and configured to engage slots 524 of top member 520. In operation, top member 520 may move up or down relative to base member 502 within the range provided by slots 524. Top member 520 also includes cutouts 528 disposed between protrusions 530 and 532 and provided to establish a motion relationship between top member 520 and bottom member 540. Bottom member 540 includes arms 542 having protrusions 544 that are received within cutouts 528 of top member 520.

Adjustable device 500 may also comprise any sizing means previously disclosed. FIGS. 5 and 5A show one embodiment of sizing means comprising a pair of arms 550 each having sizing members 552, such as protrusions or detent balls, that are configured to engage, one at a time, two or more pairs of cavities (not shown) in the underside of top member 520, such that base member 502 and bottom member 540 may be adjusted to two or more positions relative to each other. Alternatively, the protrusions may extend from the underside of top member 520 while the cavities extend into bottom member 540. Window 28 may also be provided in base member 502 such that, in each position, a different numeral from sizing area 50 may be observed therethrough.

Figure 6:
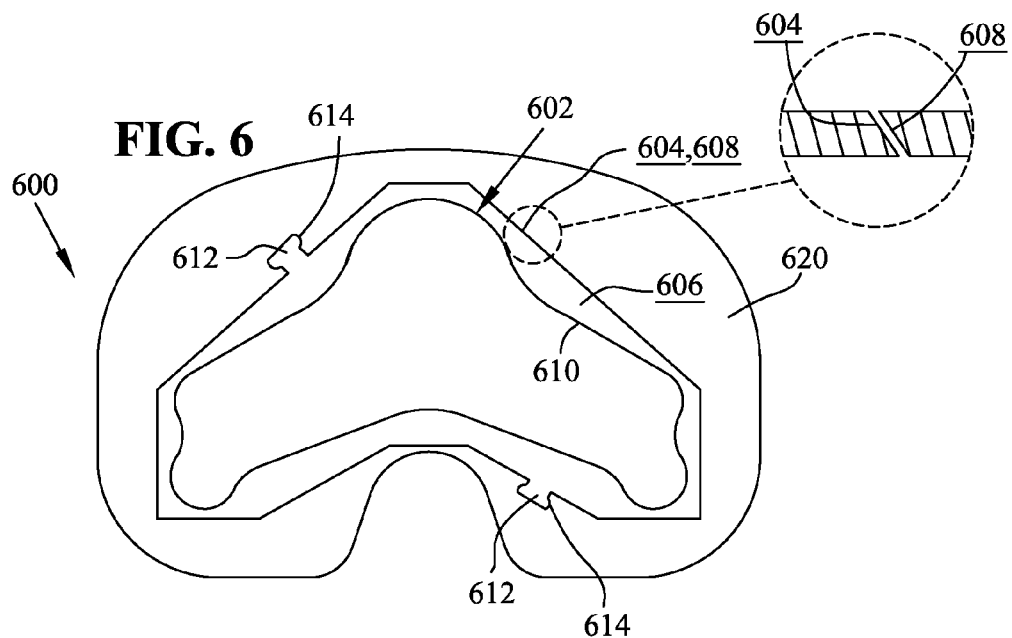
FIG. 6 is a plan view of another exemplary embodiment of an adjustable device showing a base and a sizing member.
Figure 6A:
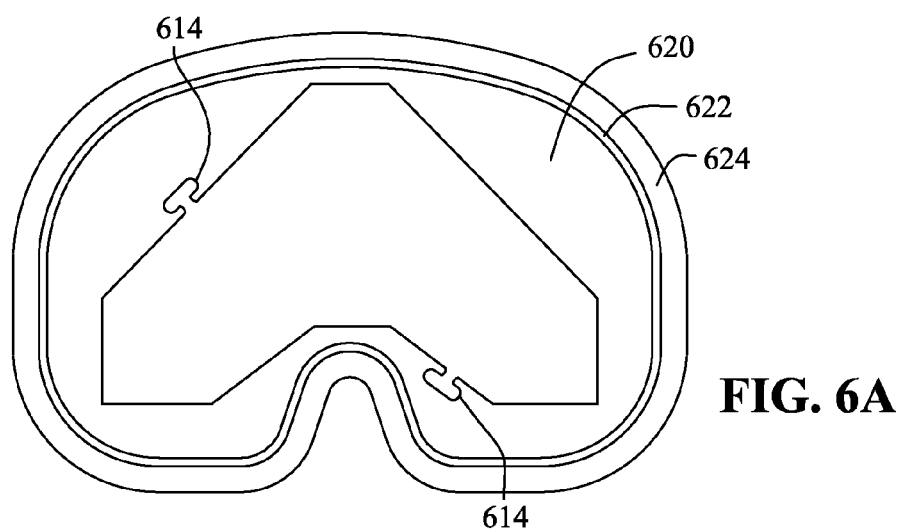
FIG. 6A is an embodiment of an integrated sizing member.

FIGS. 6 and 6A are plan views of another exemplary embodiment of an adjustable device 600. Adjustable device 600 comprises base member 602 and adjustment means including one or more detachable sizing members 620, 622, 624. Base member 602 includes aperture 610 that is sized and configured to guide the action of a medical tool or instrument such as a broach. External peripheral surface 604 of base member 602 may be angled, and internal peripheral surface 608 of sizing member 620 may be angled in a complementary manner such that when sizing member 620 is positioned over base member 602, surfaces 604, 608, engage and couple base member 602 and sizing member 620. The external peripheral surface of sizing members 620, 622, and internal peripheral surface of sizing members 622, 624, may be similarly disposed to couple sizing members to each other. Optionally, base member 602 may include hooks 612 that extend from external peripheral surface 604 and sizing member 620 may include notches 614 set into internal peripheral surface 608 that are shaped to receive protrusions 612 in a complementary manner. In an alternative embodiment, a lip (not shown) is provided extending outwardly from external peripheral surface 604 along a plane parallel to top surface 606 of base member 602 to provide a seat upon which sizing member 620 will rest when sizing member 620 is positioned over base member 602. Other lips may be similarly disposed on sizing members 620, 622, 624, to provide seats for other sizing members.

Sizing members 620, 622, 624, may be provided as an integrated member of unitary construction having weakened areas between adjacent sizing members 620, 622, 624, to enable manual separation of each sizing member 620, 622, 624 from the others. In one embodiment, the integrated member is made of plastic material and the borders between adjacent sizing members 620, 622, 624, are thinner than the rest of the thick, integrated member to create the weakened areas. In a further embodiment, the borders between adjacent sizing members 620, 622, 624, are perforated to create the weakened areas.

In operation, to adjust the size of adjustable device 600, one, two, or all three sizing members 620, 622, 624, may be secured to base member 602, and the undesired sizing members may be detached. For example, to provide adjustable device 600 in a small size, sizing members 622, 624, may be separated from sizing member 620, and sizing member 620 alone may be secured to base member 602, as shown in FIG. 6. Alternatively, to provide adjustable device 600 in a large size, sizing members 620, 622, 624, may remain connected together, and all three sizing members 620, 622, 624, may be coupled to base member 602.

Figure 7:
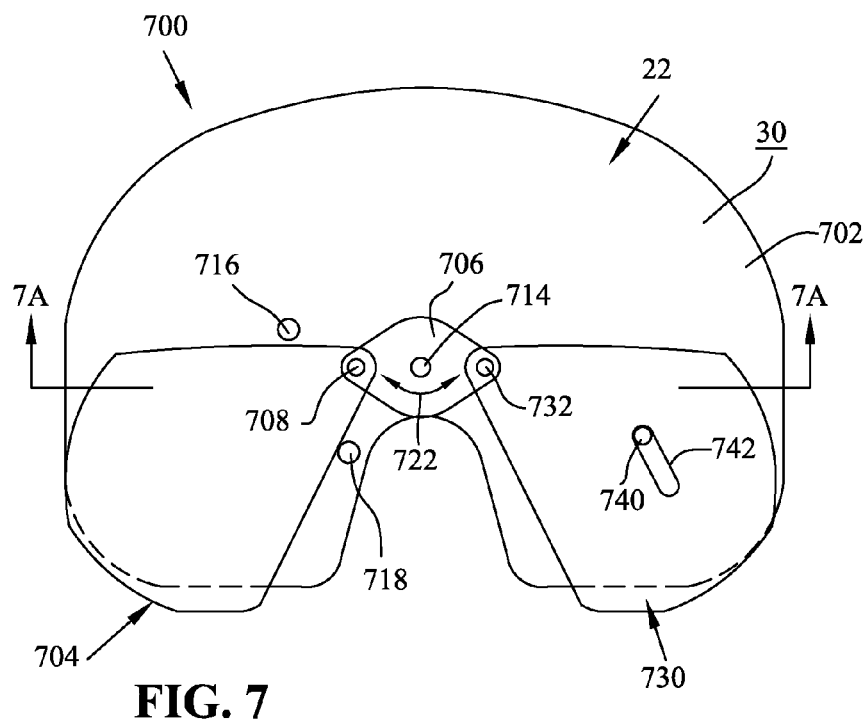
FIG. 7 is a plan view of another exemplary embodiment of an adjustable device shown in a first position.
Figure 7A:
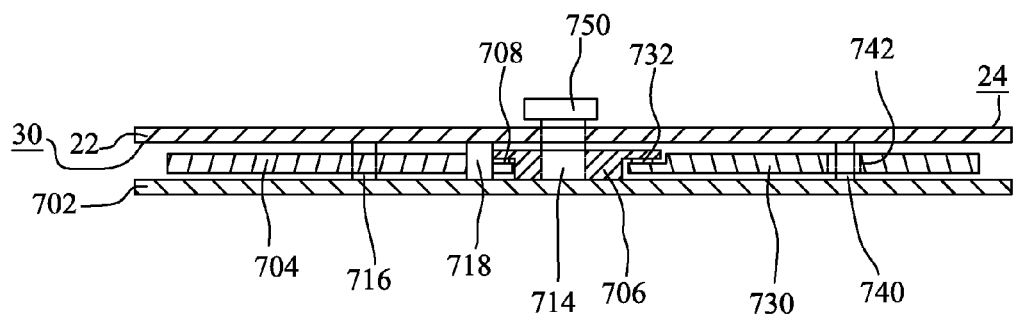
FIG. 7A is a sectional view of the adjustable device of FIG. 7.
Figure 7B:
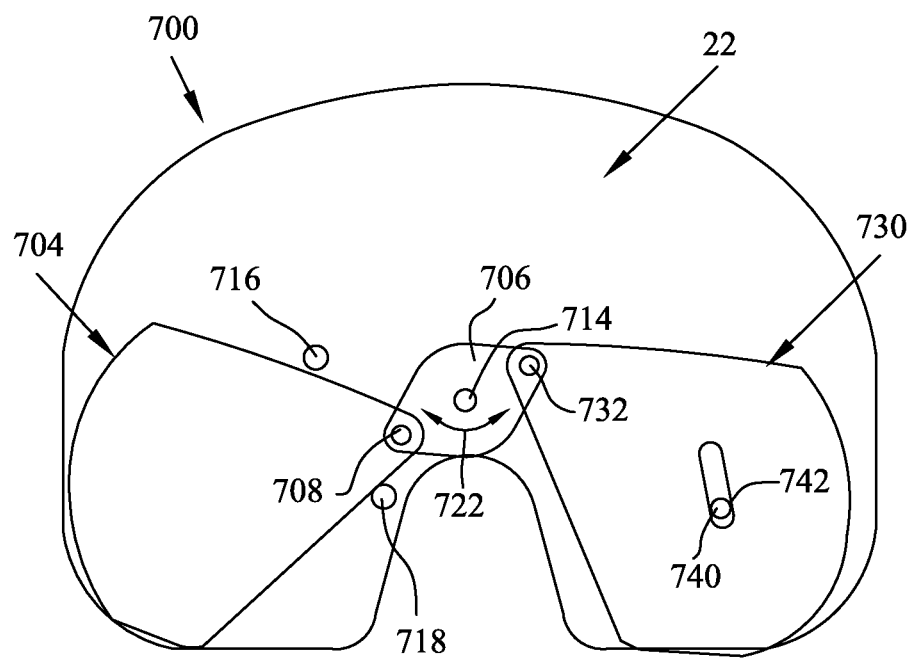
FIG. 7B is a plan view of the adjustable device of FIG. 7 shown in a second position.

FIGS. 7 and 7B are bottom plan views of an exemplary embodiment of an adjustable device 700 shown in two positions. FIG. 7A is a sectional view of the device of FIG. 7. Adjustable device 700 comprises base member 22, right member 703, and left member 730. Adjustable device 700 also comprises member 706 rotatably coupled to right and left members 704, 730, by pins 708, 732, and to base member 22 by rod 714. Base member 22 includes stops 716, 718, extending from surface 30 to control the rotation of right member 704. Base member 22 also includes pin 740 extending from surface 30 and into slot 742 of left member 730 to control the rotation of left member 730. As shown in FIG. 7B, as member 706 rotates about rod 714 in the direction of arrow 722, right member 704 is held in place by stops 716, 718, and is forced to rotate about pin 708. Also, pin 740 of base member 22 is confined to movement within slot 742 of left member 730, so left member 730 is forced to rotate about pin 732. The bottom edges of right and left members 704, 730, extend beyond base member 22 in a first position of adjustable device 700 (shown in FIG. 7) and are retracted within the outer perimeter of base member 22 in a second position of adjustable device 700 (shown in FIG. 7B). Knob 750 may be coupled, permanently or temporarily, to rod 714 to facilitate manual rotation of member 706. Optionally, base member 702 may be provided opposite to, and being shaped similarly to, base member 22 to isolate right and left members 704, 730, from contact with a bone and to enable free movement.

Figure 8:
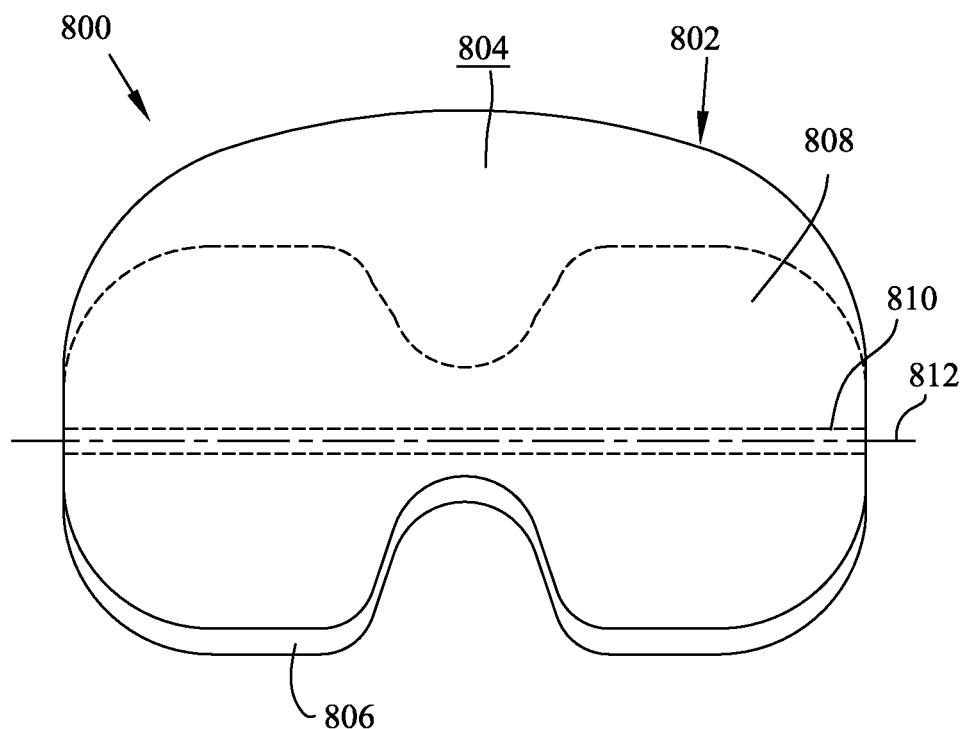
FIG. 8 is a plan view of a further exemplary embodiment of an adjustable device for adjusting a dimension of the adjustable device.

FIG. 8 is a plan view of another exemplary embodiment of an adjustable device 800. Adjustable device 800 comprises base member 802 having front surface 804 and members 806, 808, that are rotatably coupled to base member 802 by hinge 810. In operation, members 806, 808, rotate, together or independently, relative to base member 802 about centerline 812. As shown in solid in FIG. 8, members 806, 808, are positioned to extend beyond the outer periphery of base member 802 along the bottom edge of base member 802. As shown in phantom in FIG. 8, members 806, 808, may be flipped about hinge 810 such that members 806, 808, are located within the outer periphery of base member 802. It is also within the scope of the present invention that additional hinges and rotatable members may be provided and coupled to base member 802 to extend the width of adjustable device 800.

Figure 9A:
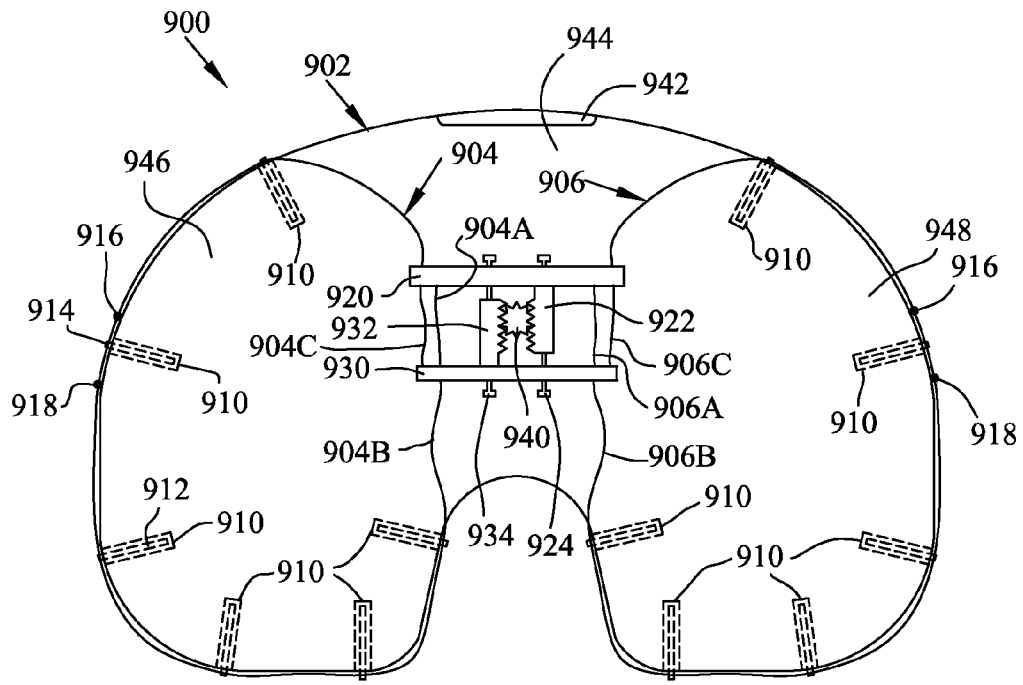
FIGS. 9A and 9B are plan views of yet another exemplary embodiment of an adjustable device shown in a first position and in a second position.
Figure 9B:
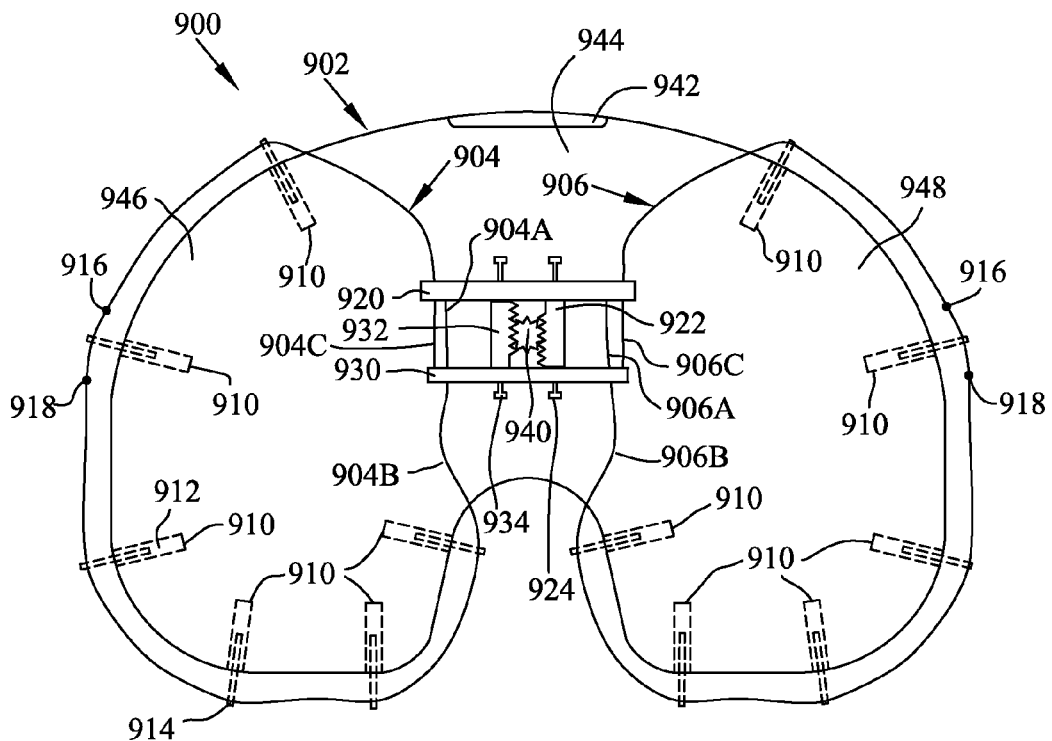

FIGS. 9A and 9B are plan views of another exemplary embodiment of an adjustable device 900. Adjustable device 900 comprises base member 902, left member 904, and right member 906. Left and right members 904, 906, may be adjusted to expand the outer periphery of adjustable device 900. Adjustment means for expanding the periphery of adjustable device 900 include top and bottom members 920, 930, top and bottom rack arms 922, 932, pinion 940, and rods 924, 934. Top member 902 is connected to top rack arm 922, and bottom member 930 is connected to bottom arm rack 932. Rods 924, 934, are coupled to base member 902 and are configured to slidingly pass through top and bottom members 920, 930, and top and bottom rack arms 922, 932.

As shown in FIG. 9A, left member 904 extends from a first end that is coupled to top member 920, clockwise around left portion 946 of base member 902, and to a second end that is coupled to bottom member 930. Specifically, beginning at the first end of left member 904 that is coupled to top member 920 and traveling clockwise, portion 904A extends from top member 920 and through an aperture (not shown) in bottom member 930, portion 904B wraps around left portion 946 of base member 902, and portion 904C extends through an aperture (not shown) in top member 920 and toward bottom member 930 until reaching the second end of left member 904 that is coupled to bottom member 930. Similarly, right member 906 extends from a first end that is coupled to top member 920, counter-clockwise around right portion 948 of base member 902, and to a second end that is coupled to bottom member 930. Specifically, beginning at the first end of right member 906 that is coupled to top member 920 and traveling counter-clockwise, portion 906A extends from top member 920 and through an aperture (not shown) in bottom member 930, portion 906B wraps around right portion 948 of base member 902, and portion 906C extends through an aperture (not shown) in top member 920 and toward bottom member 930 until reaching the second end of right member 906 that is coupled to bottom member 930.

Base member 902 defines spaced apertures 910 about its outer periphery. Each aperture 910 contains guide rod 912 that is sized to slide back and forth within its corresponding aperture 910. The outer end of each guide rod 912 includes a hole 914 through which portions 904B, 906B, of left and right members 904, 906, pass.

In operation, the size of adjustable device 900 may be adjusted by rotating pinion 940. With top member 920 and bottom member 930 spread apart as shown in FIG. 9A, the opposing ends of left and right members 904, 906, are pulled apart. Thus, the lengths of portions 904A, 904C, 906A, 906C, increase and the lengths of portions 904B, 906B, decrease. As a result, portions 904B, 906B, of left and right members 904, 906, are pulled tightly to conform substantially to the shape of base member 902. On the other hand, with top member 920 and bottom member 930 moved together as shown in FIG. 9B, the ends of left and right members 904, 906, are pulled apart. Thus, the lengths of portions 904A, 904C, 906A, 906C, decrease and the lengths of portions 904B, 906B, increase. As a result, left and right members 904, 906, are allowed to expand outwardly from base member 902, with guide rods 912 moving outwardly from apertures 910 to support and control the shape of left and right members 904, 906. It is within the scope of the present invention that left and right members 904, 906 may include stops 916, 918, disposed at selected intervals on either side of each guide rod 912 to cause expansion in a preferential shape.

While this disclosure has been described as having exemplary designs, the present disclosure can be further modified within the spirit and scope of the invention. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A sizing device for determining at least one of an anterior/posterior dimension and a medial/lateral dimension of a cross-section of a resected bone, the device comprising:
   a first member having a planar engaging surface configured to rest against the cross-section of the resected bone and an adjusting surface, opposite the engaging surface;
   a second member coupled to the first member, the second member positioned at least partially over the first member and having an adjusting surface disposed adjacent to the first member adjusting surface, the first member and the second member cooperating to define a height and a width of the device; and
   adjustment means for adjusting at least one of the height of the device to correspond to the anterior/posterior dimension of the cross-section of the resected bone and the width of the device to correspond to the medial/lateral dimension of the cross-section of the resected bone.

2. The device of claim 1, wherein the adjustment means comprises a track and a protrusion extending from one of the first and second member adjusting surfaces, the protrusion being sized and dimensioned to travel along the track.

3. The device of claim 2, wherein the track comprises an elongate channel and the protrusion comprises an elongate rail that is configured to slide along the elongate channel, whereby the first member is configured to slide relative to the second member.

4. The device of claim 2, wherein the track is rotatably coupled to the other one of the first and second member adjusting surfaces, the track having an oval or oblong shape.

5. The device of claim 1, wherein the adjustment means comprises one of a pivot pin and a hinge that rotatably couples the first member to the second member.

6. The device of claim 1, wherein the adjustment means comprises a rack and a rotatable pinion that engages and moves the rack.

7. The device of claim 1, wherein the first and second members cooperate to define a perimeter of the device.

8. The device of claim 1, wherein the adjustment means comprises a detachable portion that is removably coupled to the first and second members, the device having a first size when the detachable portion is coupled to the first and second members, and the device having a second size that is smaller than the first size when the detachable portion is detached from the first and second members.

9. The device of claim 1, wherein the first member is movably coupled to the second member, the device comprising a guide that extends from one of the first and second members to limit movement of the other one of the first and second members.

10. The device of claim 9, wherein the guide includes one of an elongate rail and a pin.

11. A sizing device for determining at least one of an anterior/posterior dimension and a medial/lateral dimension of a cross-section of a resected bone, the device comprising:
    a first member having a planar engaging surface configured to rest against the cross-section of the resected bone; and
    a second member coupled to the first member, the second member positioned at least partially over the first member and disposed opposite the engaging surface, the device having a first configuration in which the first and second members cooperate to define a first dimension measured in a direction parallel to the plane of the engaging surface and a second configuration in which the first and second members cooperate to define a second dimension measured in the same direction as the first dimension, the second dimension of the device differing from the first dimension of the device and equaling one of the anterior/posterior dimension and the medial/lateral dimension of the cross-section of the resected bone, whereby the device in the second configuration corresponds to at least one of the anterior/posterior dimension and the medial/lateral dimension of the cross-section of the resected bone.

12. The device of claim 11, wherein the first member is movably coupled to the second member to move from the first configuration to the second configuration.

13. The device of claim 12, wherein the first member is continuously movably coupled to the second member for placement in a plurality of intermediate positions between the first and second configurations.

14. The device of claim 11, further comprising a third member, wherein the first member is configured to slide relative to the second member in a first direction and the third member is configured to slide relative to the second member in a second direction transverse to the first direction.

15. The device of claim 14, wherein the third member moves independently of the first and second members.

16. The device of claim 11, wherein the second member includes a first portion and a second portion removably coupled to the first portion, the device being arranged in the first configuration when the second portion is coupled to the first portion, and the device being arranged in the second configuration when the second portion is detached from the first portion.

17. The device of claim 11, wherein the first member and the second member cooperate to define a perimeter of the device.

18. A method for determining at least one of an anterior/posterior dimension and a medial/lateral dimension of a cross-section of a resected bone, the method comprising the steps of:
provide a device including a first member and a second member, the first member and the second member cooperating to define an outer perimeter of the device;
positioning an engaging surface of the device against the cross-section of the resected bone; and
adjusting the outer perimeter of the device to correspond to at least one of the anterior/posterior dimension of the cross-section of the resected bone and the medial/lateral dimension of the cross-section of the resected bone.

19. The method of claim 18, wherein the adjusting step is performed before the positioning step.

20. The method of claim 18, wherein the adjusting step comprises simultaneously adjusting a height of the device and a width of the device.

21. The method of claim 18, wherein the adjusting step comprises independently adjusting a height of the device and a width of the device.

22. The method of claim 18, wherein the adjusting step comprises one of sliding and rotating the first member relative to the second member.

23. The method of claim 18, wherein the device further comprises a sizing member that surrounds the first and second members of the device, the adjusting step comprising one of removing and attaching the sizing member to the first and second members of the device.

24. The method of claim 18, wherein the device defines an aperture and the method further comprises the step of inserting a medical instrument through the aperture to prepare the cross-section of the bone.

25. The method of claim 18, further comprising the steps of reading a size indicia from the device and selecting a prosthesis based on the size indicia.

* * * * *